US005926405A

United States Patent [19]

Minkoff

[11] Patent Number: 5,926,405

[45] Date of Patent: *Jul. 20, 1999

[54] MULTIDIMENSIONAL ADAPTIVE SYSTEM

[75] Inventor: John Minkoff, Englewood, N.J.

[73] Assignee: Lucent Technologies, Inc., Murray Hill, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/672,008

[22] Filed: Jun. 24, 1996

[51] Int. Cl.[6] ............................ G06F 17/10; A61F 11/06

[52] U.S. Cl. .................................... 364/724.19; 381/71.1

[58] Field of Search ......................... 364/724.04, 724.19, 364/148, 574; 381/71

[56] References Cited

U.S. PATENT DOCUMENTS

| | | | |
|---|---|---|---|
| 5,309,378 | 5/1994 | Beierle | 364/574 |
| 5,410,606 | 4/1995 | Imai et al. | 381/71.11 X |
| 5,544,080 | 8/1996 | Kobayashi et al. | 364/574 |
| 5,633,795 | 5/1997 | Popovich | 364/148 |

*Primary Examiner*—Chuong Dinh Ngo

[57] ABSTRACT

A multi-dimensional adaptive method and system which can be forced to converge to any predetermined solution of interest. Disturbances are input to the system along with reference signals. Error sensors (detectors) receive the disturbances and the cancelling signals and output error signals. Compensation is determined such that the compensation converges to an arbitrary solution, is not unique and is Hermitian and positive definite.

15 Claims, 5 Drawing Sheets

MULTIDIMENSIONAL ADAPTIVE SYSTEM

BACKGROUND OF THE INVENTION

1. Field of the Invention

The present invention is directed to an adaptive system for converging solutions, and more particularly, to a multidimensional adaptive system having relatively small dimensionality that can be made to converge to solutions that could otherwise only be converged by systems having much larger dimensionality.

2. Description of the Related Art

Multi-channel feedforward adaptive systems are, for example, used to cancel noise. However, certain factors affect convergence in adaptive systems. These include the step size parameter, generally designated as $\mu$, and the effectiveness of the filtering that must be inserted into the reference-signal path at the input to a weight-iteration stage to compensate for plant transfer functions between secondary sources and detection points for a filtered-X LMS algorithm. Compensation in a reference signal path in conventional systems must be identical to the forward transfer-function between the secondary sources and the detection points. When this occurs, the adaptive filter ideally converges to the Wiener solution. In addition, feedback between the secondary sources (actuators) and the reference-signal detectors is also a factor. However, these effects can be eliminated by neutralization and are not considered further.

A one-dimensional conventional system is shown in FIG. 1. In FIG. 1, error sensors (subtractors) 20 are provided which receive disturbance or target signals D to be cancelled or reduced, and a cancelling or error reduction signal produced by the system. The error sensors 20 then produce an error signal E=PWX-D. X is a reference signal, Q* is a compensation unit 22, ΔW is an updating unit 24, W is an adaptive filter 26, and P is a physical plant 28 in which signals from the adaptive filter 26 must propagate before being input to the error sensors 20. P can vary with time. The reference signal X is input to the compensation unit 22 and the adaptive filter 26. The disturbance signals D are input to the error sensors 20. The error signals E from the error sensors 20 are input to the updating unit 24 along with compensated reference signals from the compensation unit 22. This combined signal is then input to the adaptive filter 26 along with the reference signal X and output to the physical plant 28. The physical plant 28 then outputs a signal PWX to the error sensors 20 which also receive the disturbance signals D. Thus, a feedback loop is established to compensate for the disturbance signals D, i.e., to cancel the disturbance signals.

Analysis of the one-dimensional system shown in FIG. 1, will now be given. The analysis will be carried out in frequency space with discrete Fourier transforms X(m) and D(m) of a discrete-time-series reference. Disturbance signals are given as x(n) and d(n) and $W_k(m)$ is the transfer function of the kth iteration of the adaptive-filter impulse response $w_k(n)$, given by $$X(m) = \sum_{n=0}^{N-1} x(n) e^{\frac{-i2\pi nm}{N}} \tag{1}$$

$$D(m) = \sum_{n=0}^{N-1} d(n) e^{\frac{i2\pi nm}{N}}$$

-continued $$W_k(m) = \sum_{n=0}^{N-1} w_k(n) e^{\frac{-i2\pi nm}{N}}$$

With the above formulation all results that follow are understood to refer to specific frequency pockets. Realistically, however, because of finite system bandwidth, finite ranges of frequencies should be considered.

Suppressing the discrete-frequency index m, the filter output $W_kX$ drives a secondary source L (not shown in FIG. 1) producing a response $PW_kX$ at the detection point, where the physical plant 28 generates a forward transfer function between the secondary source and the detection point which yields the squared error $|D-PW_kX|^2$. In the conventional filtered-X LMS algorithm, where X is a reference signal and LMS is the least mean square, the transfer function from the physical plant 28 is compensated in the reference signal path prior to the updating unit 24 by P. The compensation operation is denoted by Q*. The weight-iteration equation for the filtered-X LMS algorithm in frequency space takes the form $$W_{k+1}=W_k+2\mu Q^*[D-PW_kX]X^* \tag{2}$$

and after applying the above expectation operator (eq.(2))

$$\overline{W}_{k+1}=\overline{W}_k+2\mu Q^*[T-P\overline{W}_kS] \tag{3}$$

where $T=\overline{DX}^*$ is the cross spectral density between the reference and disturbance signals and $S=\overline{XX}^*$ is the cross spectral density between the reference signals themselves.

The solution to the above difference equation (3) is $$[\overline{W}_k-W_I]=[W_0-W_1][1-2\mu Q^*P\overline{|X|^2}]^k \tag{4}$$

where $W_0$ is the initial setting of the adaptive-filter transfer function at t=0 and $W_I=T/P|\overline{X}|^2$ is the ideal Wiener solution. With perfect compensation Q*=P* and the system converges if $|1-2\mu|P|^2|\overline{X}|^2|<1$, or equivalently $$\mu|P|^2\overline{|X|}^2<1 \tag{5}$$

Now let $$Q^*P=|QP|e^{i\theta}=Ae^{i\theta}$$

If the phase mismatch is zero, the system still converges if $$\mu A\overline{|X|}^2<1 \tag{6}$$

On the other hand, in the presence of phase mismatch, the compensation equation (4) becomes $$[\overline{W}_k-W_I]=[W_0-W_I][1-2\mu Ae^{i\theta}\overline{|X|^2}]^k=[W_0-W_I][1+4\mu^2A^2[\overline{|X|^2}]^2-4\mu A\overline{|X|}^2\cos\theta]^{k/2}e^{ik\phi} \tag{7}$$

where $$\phi = \tan^{-1}\left[\frac{2\mu A\overline{|X|^2}\sin\theta}{1-2\mu A\overline{|X|^2}\cos\theta}\right] \tag{8}$$

If $|\theta|>\pi/2$, the magnitude of the term within the brackets in equation (7) exceeds unity and the system will not converge. Even if $|\theta|<\pi/2$, phase mismatch can be quite serious, and in this case, convergence $$\mu A\overline{|X|}^2<\cos\theta \tag{9}$$

requiring, compared with equation (6), possibly smaller values of $\mu$ to insure convergence. Also, even if the condition for convergence is met, the convergence time can be significantly increased since the term in square brackets in equation (7) increases with θ. The results are summarized in FIG. 2, including FIGS. 2A and 2B. As shown, if there is no phase mismatch the term $1-2\mu Q^\dagger P|X|^2$ in equation (4) is real. Therefore, the phase of $(\overline{W_k}-W_0)$ remains unchanged during convergence and $\overline{W_k}$ follows the shortest straight-line path from $W_0$ to $W_I$ as shown in FIG. 2A. This is an essential feature of the filtered-X LMS algorithm. However, if there is phase mismatch the system may never converge and, at best, convergence will be slowed down as shown in FIG. 2B, with $\overline{W}_k$ taking a circuitous route, as determined by φ, through the complex plane from $W_0$ to $W_I$. Although mismatch in the compensation amplitude is tolerable, accurate phase compensation is critical.

Further, when a multidimensional system is employed, rather than a one-dimensional system as set forth above, the system can become very large to the point of becoming prohibitively large, expensive, less efficient and almost impossible to cancel noise.

SUMMARY OF THE INVENTION

The present invention provides a multi-dimensional adaptive system and method for use in a large complex system, having many disturbances, which converges to an arbitrary solution. A compensator is provided to force the adaptive system to converge to any solution of interest. An updating unit for modifying and updating signals is employed. The multi-dimensional adaptive method and system of the present invention is smaller and more efficient than prior art systems.

The above-mentioned features and advantages are achieved by employing a multi-dimensional adaptive system for which there is a source of reference signals, actuators for producing cancelling signals and detectors for receiving disturbance signals and the cancelling signals and outputting error signals. A compensation unit receives the reference signals and outputs compensated reference signals to force the adaptive system to converge to any solution of interest. An adaptive filter receives the compensated reference signals, error signals and reference signals and outputs signals to drive the actuators. The adaptive filter unit includes an updating unit and an adaptive filter which outputs signals to the actuators.

The method of the present invention includes receiving reference signals, receiving disturbance signals, producing cancelling signals and generating error signals based on the differences between the cancelling signals and the disturbance signals. The reference signals are then compensated to force the adaptive system to converge to any desired solution. The reference signals, compensated reference signals and error signals are then updated. Disturbances in the system are then cancelled.

In addition, the reference signals and the disturbance signals exhibit coherency. Further, the method includes providing detectors for receiving the disturbance signals.

These objects, together with other objects and advantages which will be subsequently apparent, reside in the details of construction and operation as more fully described and claimed, reference being had to the accompanying drawings forming a part hereof, wherein like reference numerals refer to like parts throughout.

DESCRIPTION OF THE PREFERRED EMBODIMENTS

The present invention is a multi-dimensional adaptive system which can be forced to converge to any arbitrary solution of interest. As is well known, compensation in the reference signal path in conventional feed forward systems must be identical to the forward transfer-function between the secondary sources and the detection points such that the adaptive filter ideally converges to the Wiener solution. As noted above, conventional systems employ compensation filters $P^\backslash_N$ in the feedforward reference signal path. Ideally, the filters are identical to actuator-to-error-sensor transfer functions. That is, in conventional systems the transfer functions representing the physical plant constitute the compensation in the reference signal path. Further, in conventional systems, Q=P and $Q^\dagger P=P^\dagger P$, which is Hermitian and positive definite. These are necessary requirements for convergence.

The present invention, however, appropriately alters the compensation of the conventional system and forces the adaptive system to converge to any predetermined solution of interest. This is achieved by employing an alternate form of compensation. That is, compensation $Q^\dagger$ is used. The compensation $Q^\dagger$, in general, has transfer functions different from that of the transfer functions representing a physical plant. The physical plant receives a signal from actuators (secondary sources). In addition, the present invention employs the filtered-X LMS algorithm. The compensation $Q^\dagger$ is chosen to force the adaptive system to converge to any desired ideal solution $W_D$.

Therefore, the present invention can be used, for example, to cancel noise at many locations in a large room using only a small number of error signals. Thus, the system has relatively small dimensionality compared to prior art systems.

Figure 1:
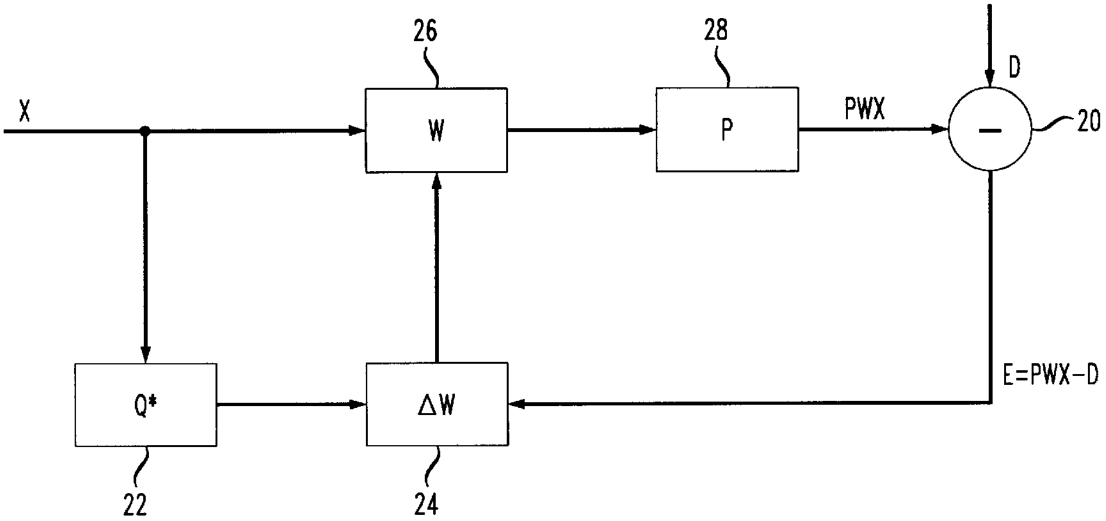
FIG. 1 PRIOR ART
FIG. 1 is a block diagram of a conventional one-dimensional system.
Figure 2B:
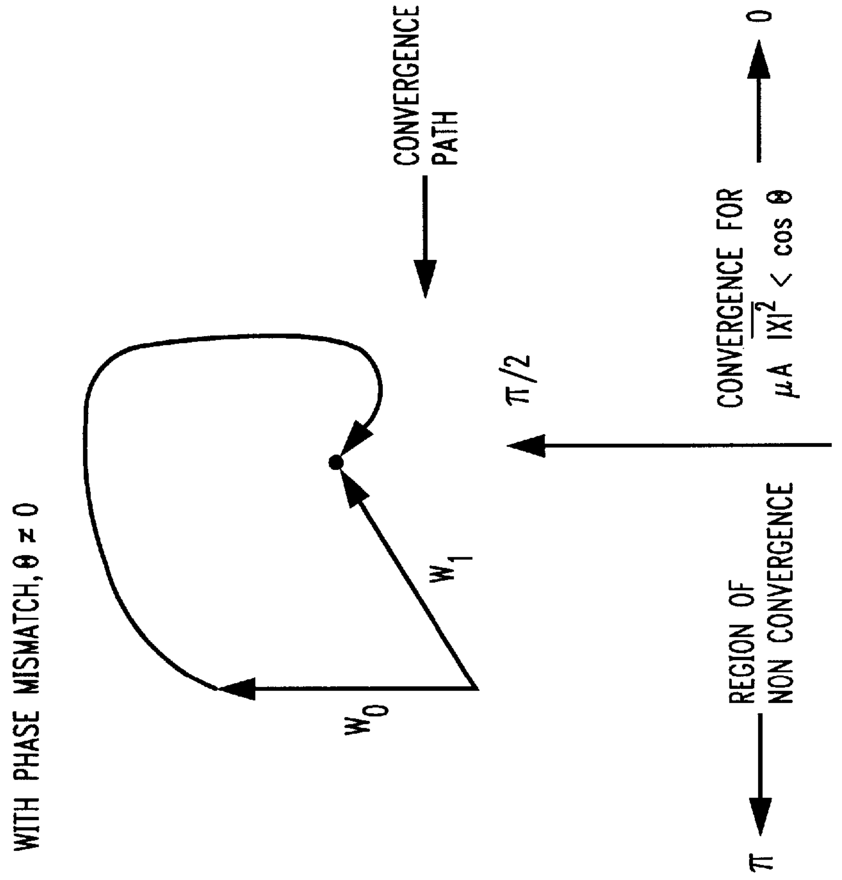
FIG. 2B PRIOR ART
FIG. 2A and FIG. 2B, are diagrams of the effects of compensation mismatch for a one-dimensional system.
Figure 2A:
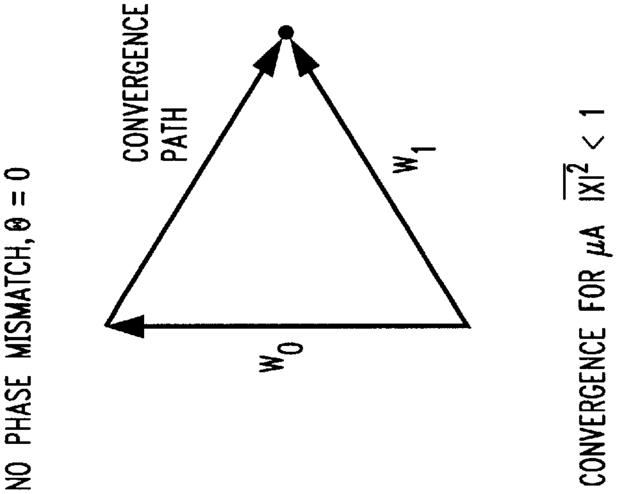
FIG. 2A PRIOR ART
Figure 3:
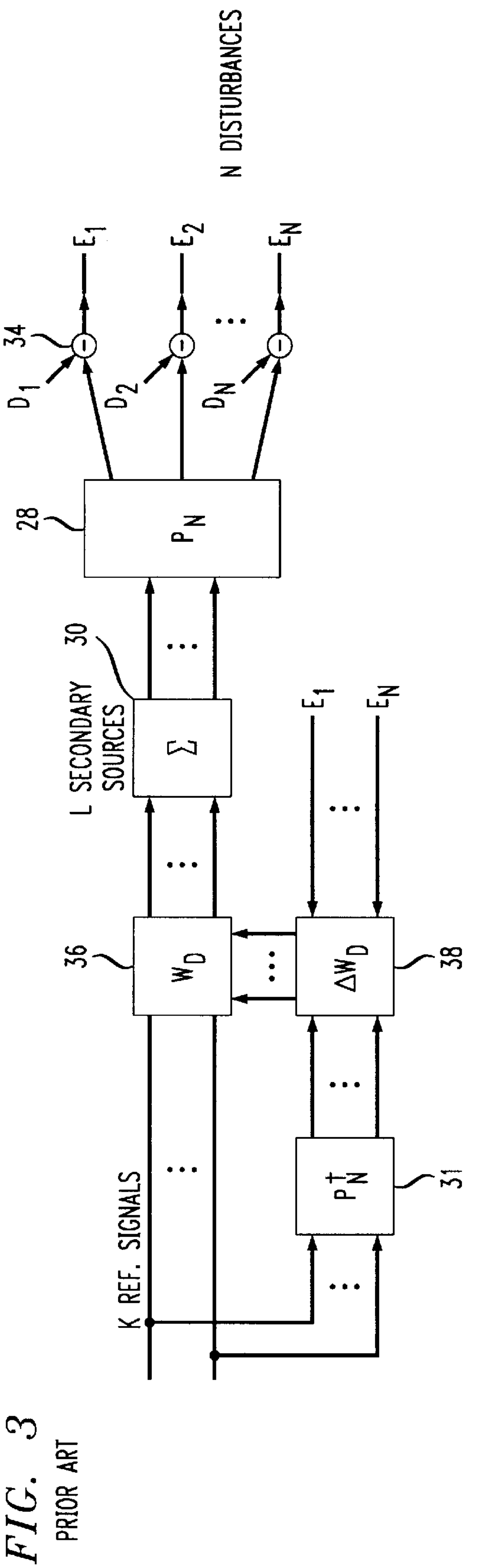
FIG. 3 PRIOR ART
FIG. 3 is a block diagram of a conventional ideal desired system.

The present invention will now be explained with respect to the drawings. An ideal desired conventional multi-dimensional system is shown in FIG. 3. In general, the ideal desired conventional system has K reference signals, L secondary sources (actuators) 30 and N disturbances and detection points. Compensation unit $P_N^\dagger$ 31, error sensors 34, adaptive filter 36 and updating unit 38 are shown. The following also apply:

$\vec{X}$ is a KX1 vector of reference signals;

$\vec{D}$ is an MX1 vector of disturbances;

P is an MXL matrix of transfer functions between the secondary sources L and the M disturbances;

Q is an MXL compensation matrix;

W is an LXK matrix of adaptive filter transfer functions between the reference signals and secondary sources;

$T=\overline{\vec{D}\,\vec{X}^\dagger}$ is an MXK matrix of cross spectral densities between the reference signals and the disturbances; and $S=\overline{\vec{X}\ \vec{X}^{\dagger}}$ is a KXK matrix of cross spectral densities between the reference signals.

A weight-iteration equation in frequency space takes the form $$\overline{W}(k+1)=\overline{W}(k)+2\mu Q^{\dagger}[T-P\overline{W}(k)S] \quad (10)$$
$$=\overline{W}(k)2\mu Q^{\dagger}P\overline{W}(k)S+2\mu Q^{\dagger}T$$

Where, with perfect compensation, i.e., in the ideal desired conventional system, Q=P and $Q^{\dagger}P=P^{\dagger}P$ which is Hermitian and positive definite as is S. Therefore, S and $P^{\dagger}P$ can be written as $$P^{\dagger}P=V_p\Lambda_pV_p^{-1}$$
$$S=V_s\Lambda_sV_s^{-1} \quad (11)$$

where $V_p$ and $V_s$ are unitary matrices whose columns are the eigenvectors of $P^{\dagger}P$ and S, and where $\Lambda_p$ and $\Lambda_s$ are diagonal matrices whose entries are the positive real eigenvalues $\pi_i$ and $\sigma_i$ of $PP^{\dagger}$ and S.

It is assumed that P is full rank and therefore, referring to eq. 10

$$2\mu P^{\dagger}T=2\mu(P^{\dagger}P)W_IS \quad (12)$$

where $$W_I=[P^{\dagger}P]^{-1}P^{\dagger}TS^{-1} \quad (13)$$

is the ideal Weiner solution for the multi-dimensional case. By substituting eq. 11 into eq. 10 and multiplying from the left by $V_p^{-1}$ and multiplying from the right by $V_s$, eq. 10 becomes $$\hat{W}(k+1)=\hat{W}(k)-2\mu\Lambda_p\hat{W}(k)\Lambda_s+2\mu\Lambda_p\hat{W}_I\Lambda_s \quad (14)$$

where $$\hat{W}=V_p^{-1}WV_s \quad (15)$$

But the ijth element of $\Lambda_p\ \hat{W}\Lambda_s$ is $$[\Lambda_p\hat{W}\Lambda_s]_{ij}=\pi_i\sigma_j\hat{W}_{ij} \quad (16)$$

where $\hat{W}_{ij}$ is the ijth entry of $\hat{W}$. Thus, a simple difference equation for each element of $\hat{W}$ is $$\hat{W}(k+1)_{ij}=\hat{W}(k)_{ij}-2\mu\pi_i\sigma_j\hat{W}(k)_{ij}+2\mu\pi_i\sigma_j\hat{W}_{Iij} \quad (17)$$

with the solution $$[\hat{W}(k)_{ij}-\hat{W}_{Iij}]=[\hat{W}(O)_{ij}-\hat{W}_{Iij}][1-2\mu\pi_i\sigma_j]^k \quad (18)$$

where $\hat{W}_{Iij}$ is the i,jth element of eq. 13. Although $\hat{W}$ given by eq. 15 represents the system transfer function transformed to a different coordinate system, the rate of convergence is identical to that of W. Therefore convergence of $W_{ij}$ requires $$|1-2\mu\pi_i\sigma_i|<1,$$

or equivalently $$\mu\pi_i\sigma_i<1 \quad (19)$$

With perfect compensation the inequality $\mu\pi_i\sigma_i<1$ can always be satisfied since $\pi_i$ in this case are real and positive and $\sigma_i$ are always real and positive. With imperfect compensation the convergence properties of the system will depend on the eigenvalues of $Q^{\dagger}P$ which must be both Hermitian and positive definite for convergence. In the multi-dimensional case these criteria replace the foregoing condition regarding amplitude and phase compensation for the one-dimensional case. Effects of compensation errors in the multi-dimensional case must therefore be evaluated by calculating the eigenvalue sof $Q^{\dagger}P$, determining which, if any, are negative and/or complex, and assessing the effects by employing eqs. 7 or 19.

The ideal desired conventional system in FIG. 3 has perfect compensation. An ideal adaptive filter transfer function $W_D$ is given by $$W_D=[P^{\dagger}_NP_N]^{-1}P^{\dagger}_NT_DS^{-1} \quad (20)$$

where $P_N$ is the N×L matrix of transfer functions from the L secondary sources 30 to the N detection points and $$T_D=\overline{\vec{D}_N\ \vec{X}^{\dagger}} \quad (21)$$
$$S=\overline{\vec{X}\ \vec{X}^{\dagger}}$$

where $\vec{D}_N$ is the N×1 vector of disturbances and $\vec{X}$ is the KX1 vector of reference signals.

Figure 4:
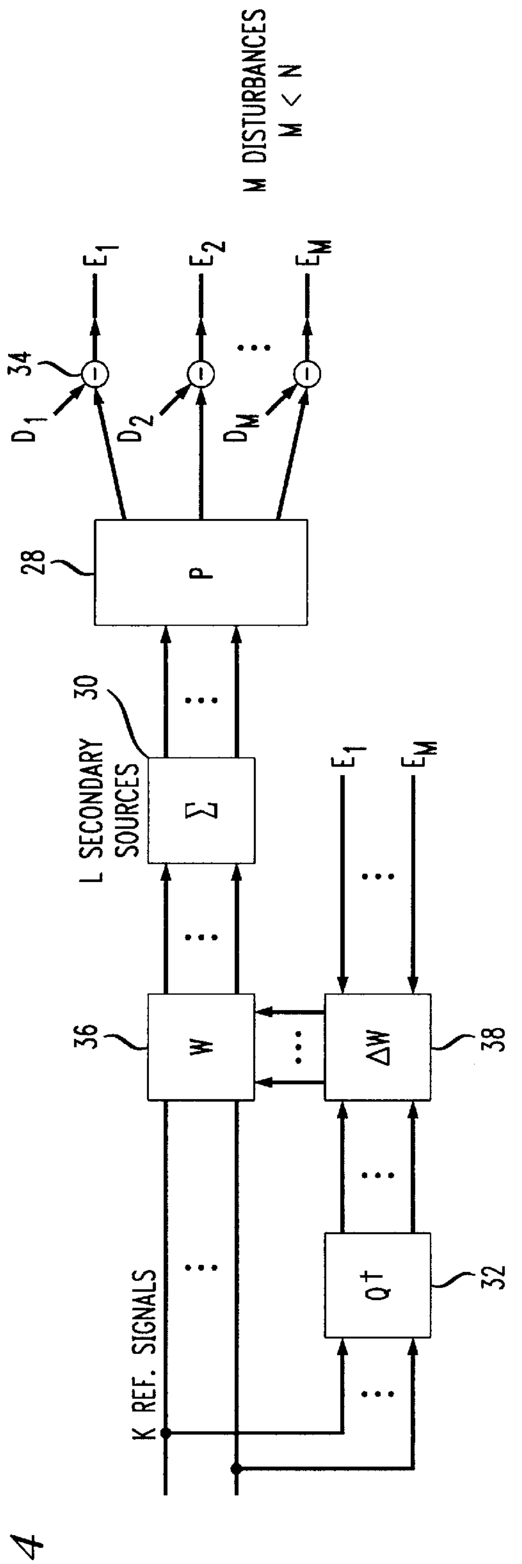
FIG. 4 is a block diagram of a multi-dimensional adaptive system according to a first embodiment of the present invention.

FIG. 4 is a block diagram of a multi-dimensional adaptive system according to a first embodiment of the present invention. In FIG. 4, like reference numerals in FIG. 3 refer to like parts in FIG. 4. FIG. 4 shows the physical system in which compensation $Q^{\dagger}$ in a compensation unit 32 is chosen to force an adaptive system to converge to any desired ideal solution $W_D$. This is of interest for controlling, for example, noise levels at many points in a very large room which would normally require a microphone at each of many desired detection points. A large number of error signals would be generated and would require appropriate signal paths, processing electronics, etc. The number of such points could be so large that implementation of such a system would be prohibitive. However, with the proper choice of compensation $Q^{\dagger}$ in the compensation unit 32, control over a very large volume can be implemented by physically controlling the disturbances as a small subset of the total number of desired detection points.

As an example, the present invention can employ secondary sources (actuators) 30 to produce, for example, sound waves throughout the room. Detectors (not shown) pick up the sound waves. In FIG. 4, the physical plant (structure) 28 can be mechanical, air, etc. First characteristics of the physical plant 28 are measured. Error sensors 34, for example, microphones, receive a cancelling signal PWX along with the disturbances $D_M$. The error sensors 34 output error signals $E_M$, $E_M$=PWX-$D_M$. Reference signals K are input to an adaptive filter 36 and to the compensation unit 32. The reference signals bear some relationship to the disturbances. The reference signals and the disturbances can come from the same source but can have different paths so that they are related (i.e., coherent) but are not the same. An updating unit 38 receives the error signals $E_M$ from the error sensors 34 along with compensated reference signals from the compensation unit 32. The updating unit 38 continuously modifies the adaptive filter 36 to drive the error signals to a minimum. The adaptive filter 36 generates canceling signals and outputs the canceling signals to the secondary sources (actuators) 30. The actuators 30, coupled between the adaptive filter 36 and the error sensors 34 by the transfer functions which characterize the physical plant 28, output source signals. The actuator outputs modified by the physical plant 28 are input to the error sensors 34 to cancel the disturbances. That is, the error sensors 34 output the difference between the disturbance signals and the actuator signals modified by the physical plant 28, as error signals. These error signals are fed back to the updating unit 38 by the system. Therefore, the present invention continually provides adjustment to obtain signals close to the disturbances, to cancel the disturbances and to minimize errors.

The determination of Q in the compensation unit 32 requires calculating $W_D$. The calculation of $W_D$ is not explained in this application, but is well known and can be obtained using various methods, such as, for example, eq. 20. Because Q is not unique there are infinite solutions. However, Q must be chosen such that $Q^\dagger P$ is Hermitian and positive definite otherwise the system will not converge. Although the transfer functions must be known for all the locations that, for example, noise is to be cancelled, a detector (for example, a microphone) is not necessary for each location.

The physical system shown in FIG. 4 has the same number of reference signals K and actuators (secondary sources) 30, but has M disturbances where M<N, and an M×L forward transfer function matrix P. As noted above, the problem is choosing Q such that W(k) converges to $W_D$, the ideal transfer function. Referring to eq. 10, it is observed that in a conventional system with perfect compensation, convergence takes place when $$\overline{\Delta W}=\overline{P^\dagger(T-PW(k)S)}=0 \tag{22}$$

which requires $$\overline{W(k)}\rightarrow\overline{W}_I=[P^\dagger P]^{-1}\overline{P^\dagger TS^{-1}} \tag{23}$$

where $W_I$ is the ideal Weiner solution. If compensation is implemented by $Q^\dagger \neq P^\dagger$, the weight iteration equation becomes $$W(k+1)=W(k)+2\mu Q^\dagger[T-PW(k)S] \tag{24}$$

which is the same as eq. 10. Thus, the system can be forced to converge to any arbitrary desired solution $W_D$ if the selected Q satisfies $$Q^\dagger[T-PW_DS]=0 \tag{25}$$

This occurs because the quadratic error surface has only a single minimum. If eq. 25 is satisfied, then $W_D$ is the only stable point of convergence.

The matrix Q includes L complex column vectors qi. Eq. 25 is therefore equivalent to the sets of equations $$Bq_i=0,\ i=1,2,\ \ldots\ L \tag{26}$$

where $$B=[T-PW_DS]^\dagger \tag{27}$$

is KXM, is full rank, and of course cannot be square because if it is, there is only the trivial solution qi=0 for all i. The system described by eq. 26 contains LK equations in LM unknowns, with LM>LK. Therefore, qi are under determined. There are, however, certain necessary constraints that provide additional equations for qi. Specifically, referring to eq. 24 and eqs. 10–19, if Q can be chosen so that $Q^\dagger P$ is Hermitian and positive definite, it can be represented as $$Q^\dagger P=V\Lambda V^{-1} \tag{28}$$

where Λ is a diagonal matrix of real positive eigenvalues $\lambda_i$ of $Q^\dagger P$. Convergence of eq. 24 is then guaranteed, referring to eq. 18, with the solution $$[\hat{W}(k)_{ij}-\hat{W}_{Dij}]=[\hat{W}(0)_{ij}-\hat{W}_{Dij}][1-2\mu\lambda_i\sigma_j]^k \tag{29}$$

where, as set forth above, $$\hat{W}_D=V^{-1}W_DV_s \tag{30}$$

and the condition for convergence is $$\mu\lambda_i\sigma_i<1 \tag{31}$$

To determine how to choose Q so that eq. 28 is satisfied will now be explained. It is essential that L<M and P cannot be square. A simple choice, which is not unique, is, for example, to let Q satisfy $$Q^\dagger P=P^\dagger P \tag{32}$$

where P must be full rank and $P^\dagger P$ is positive definite and Hermitian. Equation 32 also provides causality. The present invention, however, is not limited to the solution in eq. 32. This is just one possibility. If P is square then eq. 32 can only be satisfied by P=Q which is a conventional solution. Since $P^\dagger P$ is L×L, eq. 32 provides $L^2$ constraint equations for qi as well as satisfying the necessary conditions for convergence. Thus, employing eq. 32 in eq. 31, eq. 31 becomes identical to eq. 19 and $W_D$ replaces $W_I$.

This solution is optimal in that the rate of convergence is identical to what would be achieved if conventional compensation were employed. It also provides for causality as set forth above. If, for example, M=5, K=2 and L=2, then $$Q=[q_1,q_2] \tag{33}$$

$$P=[p_1,p_2]$$

and eq. 32 becomes $$\begin{bmatrix} q_1^\dagger p_1 & q_1^\dagger p_2 \\ q_2^\dagger p_1 & q_2^\dagger p_2 \end{bmatrix} = \begin{bmatrix} p_1^\dagger p_1 & p_1^\dagger p_2 \\ p_2^\dagger p_1 & p_2^\dagger p_2 \end{bmatrix} \tag{34}$$

where $$q_i = \begin{bmatrix} q_{i1} \\ q_{i2} \\ q_{i3} \\ q_{i4} \\ q_{i5} \end{bmatrix} \quad p_i = \begin{bmatrix} p_{i1} \\ p_{i2} \\ p_{i3} \\ p_{i4} \\ p_{i5} \end{bmatrix} \tag{35}$$

Therefore, taking into consideration La Place transforms, the individual elements of the matrices in eq. 34 satisfy relationships for the (1,1) terms as follow, $$q_{11}^{(-s)}p_{11}^{(s)}+q_{12}^{(-s)}p_{12}^{(s)}+q_{13}^{(-s)}p_{13}^{(s)}+q_{14}^{(-s)}p_{14}^{(s)}+q_{15}^{(-s)}p_{15}^{(s)}$$

$$=p_{11}^{(-s)}p_{11}^{(s)}+p_{12}^{(-s)}p_{12}^{(s)}+p_{13}^{(-s)}p_{12}^{s)}+p_{14}^{(-s)}p_{14}^{(s)}+p_{15}^{(-s)}p_{15}^{(s)} \tag{36}$$

because all the relevant time functions are real. Therefore $p_{11}(s)=p_{11}^*(s)$, $q_{11}(s)=q^*_{11}(-s)$, etc., where, $s=\sigma+i2\pi f$. Since the transfer functions $p_{ij}(s)$represents physical measurements, the associated impulse responses are causal and the poles of $p_{ij}(s)$ are all in the left-half of the s plane and the poles of $p_{ij}(-s)$ are all in the right-half of the s plane. Thus, the locations of all poles and zeros on the left-hand side of eq. 36 must be identical to all poles and zeroes on the right-hand side of eq. 36, except that all the poles of $q_{ij}(-s)$ must be in the right-half plane and represent causal impulse responses. The exception to this being if $p_{ij}(s)$ happens to have zeroes in the left-half plane in exactly the same locations as poles of $q_{ij}(-s)$ in the left-half plane. This would violate causality for $q_{ij}(s)$. In the event that this situation occurs, the error sensors can be relocated to obtain suitable $p_{ij}(s)$. Continuing, if $$(B)_{ij}=b_{ij}$$

The following equations result $$b_{11}q_{11}+b_{12}+q_{12}+b_{13}q_{13}+b_{14}q_{14}+b_{15}+q_{15}=0$$

$$b_{21}q_{11}+b_{22}q_{12}+b_{23}q_{13}+b_{24}q_{14}+b_{25}q_{15}=0$$

$$p^*_{11}q_{11}+p^*_{12}q_{12}+p^*_{13}q_{13}+p^*_{14}q_{14}+p^*_{15}q_{15}=|p_1|^2 \tag{37}$$

$$p_{21}{}^*q_{11}+p_{22}{}^*q_{12}+p^*_{23}q_{12}+p^*_{24}q_{14}+p_{25}q_{15}=p^{\dagger}{}_1p_2$$

and a similar set of equations for $q_{2j}$s results. Therefore, eq. 37 and the equivalent set for $q_2$ satisfy eq. 26 as well as all the necessary conditions for convergence. It should be noted that in this example, the number of unknowns, 2×5=10, exceeds the number of equations (8) by two (2) and thus, the values of one of the $q_{ij}$ and one of the $q_{2j}$ can be assigned an arbitrary value. There does not appear to be any reason why this is not perfectly satisfactory, and could even be advantageous. However, a unique solution for $q_{ij}$s can also be obtained by, for example, increasing either K or L by 1, yielding , for example, when L is increased by one, the following constraint equations $$\begin{matrix} q^{\dagger}{}_1p_1 & q^{\dagger}{}_1p_2 & q^{\dagger}{}_1p_3 & & p^{\dagger}{}_1p_1 & p^{\dagger}{}_1p_2 & p^{\dagger}{}_1p_3 \\ q^{\dagger}{}_2p_1 & q^{\dagger}{}_2p_2 & q^{\dagger}{}_2p_3 & = & p^{\dagger}{}_2p_1 & p^{\dagger}{}_2p_2 & p^{\dagger}{}_2p_3 \\ q^{\dagger}{}_3p_1 & q^{\dagger}{}_3p_3 & q^{\dagger}{}_3p_3 & & p^{\dagger}{}_3p_1 & p^{\dagger}{}_3p_2 & p^{\dagger}{}_3p_3 \end{matrix} \tag{38}$$

There now are 15 unknowns, 6 equations of the form $Bq_{ij}=0$, and 9 constraints in eq. 38. Generally, the following must always apply $$M \geq K+L \tag{39}$$

and for a unique solution for Q, $LM-LK=L^2$ or the following $$M=K+L \tag{40}$$

must apply. If M<K+L, then $q_{ij}$s are over determined and there is only a least-square solution which may be unsatisfactory.

Figure 5:
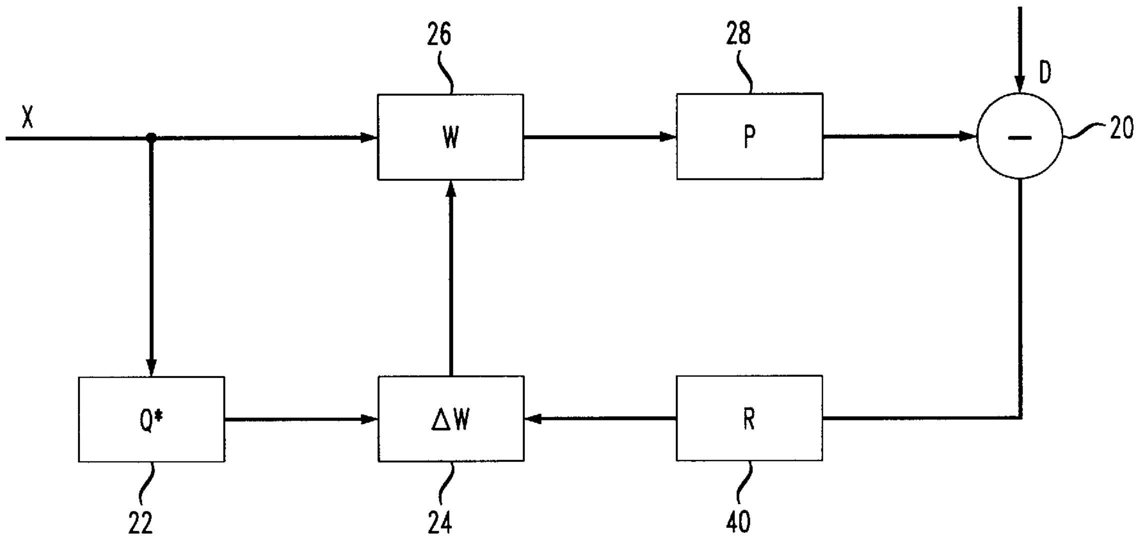
FIG. 5 is a block diagram of a multi-dimensional system according to a second embodiment of the present invention.

Alternatively, the following scheme can be considered to force the system to converge to an arbitrary desired solution. A block diagram of a second embodiment according to the present invention is shown in FIG. 5. In FIG. 5, conventional compensation Q* in a conventional compensation unit 22 is used along with R in the reference signal path, R being a transformation on error signals which occurs in a transformation unit 40. The compensation can be modified by using Q as in the first embodiment or using P and adding R for providing compensation in the error signal path. The weight-iteration operation employs a transformed error vector $$\vec{E}=R\vec{E} \tag{41}$$

where, as set forth above, $$\vec{E}=(\vec{D}-PW\vec{X}) \tag{42}$$

and the square, M×M linear tranformation R is chosen so that the system converges to $W_D$ in eq. 20. That is, R is solved for. The weight iteration equation 10 now becomes $$W(k+1)=W(k)+2\mu P^{\dagger}R(T-PW(k)S) \tag{43}$$

where R must satisfy $$P^{\dagger}R(T-PW_DS)=0 \tag{44}$$

Comparing eq. 43 with eq. 10 or eq. 24, then $$P^{\dagger}R=Q^{\dagger} \tag{45}$$

and $$P^{\dagger}RP=Q^{\dagger}P \tag{46}$$

Since $Q^{\dagger}P$ must be Hermitian and positive definite, then R must also be Hermitian. Equations 43, 44, and 46 are equivalent to equations 24, 25 and 28. As set forth above in eq. 32, a simple solution is to let R satisfy $$P^{\dagger}RP=P^{\dagger}P \tag{47}$$

then, $$(P^{\dagger}RP)=(P^{\dagger}RP)^{\dagger}=P^{\dagger}R^{\dagger}P \tag{48}$$

where R is Hermitian. Also, for any arbitrary vector $\vec{y}$ let $\vec{z}=P\vec{y}$ and $$\vec{y}^{\dagger}P^{\dagger}RP\vec{y}=\vec{z}^{\dagger}R\vec{z}=\vec{y}^{\dagger}P^{\dagger}P\vec{y}=|z|^2>0 \tag{49}$$

where R is also positive definite.

If P is square, eq. 47 is satisfied only when R is equal to the identity. This defeats the purpose of the present invention. Therefore, as set forth above, P must be rectangular for the present system to work. The quantity $\vec{\xi}$ being minimized is $$\vec{\xi}=\overline{\vec{E}R\vec{E}^{\dagger}} \tag{50}$$

It is easily verified that taking the gradient of eq. 50 with respect to W yields eq.43. Equation 50 is real and positive since R is Hermitian and positive definite. Thus, a quadratic error surface with a single minimum for W, which is desirable in adaptive systems, is obtained. Comparing this embodiment with the first embodiment, it would appear that it would be simpler to calculate Q from eqs. 25 and 32 than to calculate R from eqs. 44 and 47. Of course the system operation is identical for the two cases since the weight-iteration process is exactly the same for both. An observer would have no way of telling whether the first or second embodiment is being used. The results, however, are useful for defining the explicit quantity in eq. 50 that is being minimized in achieving a forced solution and also for establishing the existence of the single minimum quadratic error surface for W in the forced solution case. However, minimizing the quantity $\vec{\xi}$ in eq. 50 may not minimize the conventional penalty function $\vec{E}^{\dagger}\vec{E}$. Using eq. 47 it is easily shown that $$\overline{\vec{E}^{\dagger}R\,\vec{E}^{\dagger}}-\overline{E^{\dagger}E}=\overline{\vec{D}^{\dagger}R}\quad\overline{\vec{D}-\vec{D}^{\dagger}\vec{D}} \tag{51}$$

As set forth above, the dependence of the convergence characteristics of adaptive systems employing the filtered-X-LMS algorithm on reference signal forward-path compensation have been shown. Necessary criteria for convergence for one-dimensional and multi-dimensional systems have been derived. In the present invention, the proper choice of reference path compensation for an adaptive system can be forced to converge to any arbitrary solution of interest. The system and method of the present invention allow for a smaller, more efficient system which is less expensive than prior art systems and makes noise cancellation possible in most cases.

The foregoing is considered as illustrative only of the principles of the invention. Further, since numerous modifications and changes will readily occur to those skilled in the art, it is not desired to limit the invention to the exact construction and applications shown and described, and accordingly, all suitable modifications and equivalents may be restored to, falling within the scope of the invention and the appended claims and their equivalents.

Figure 6:
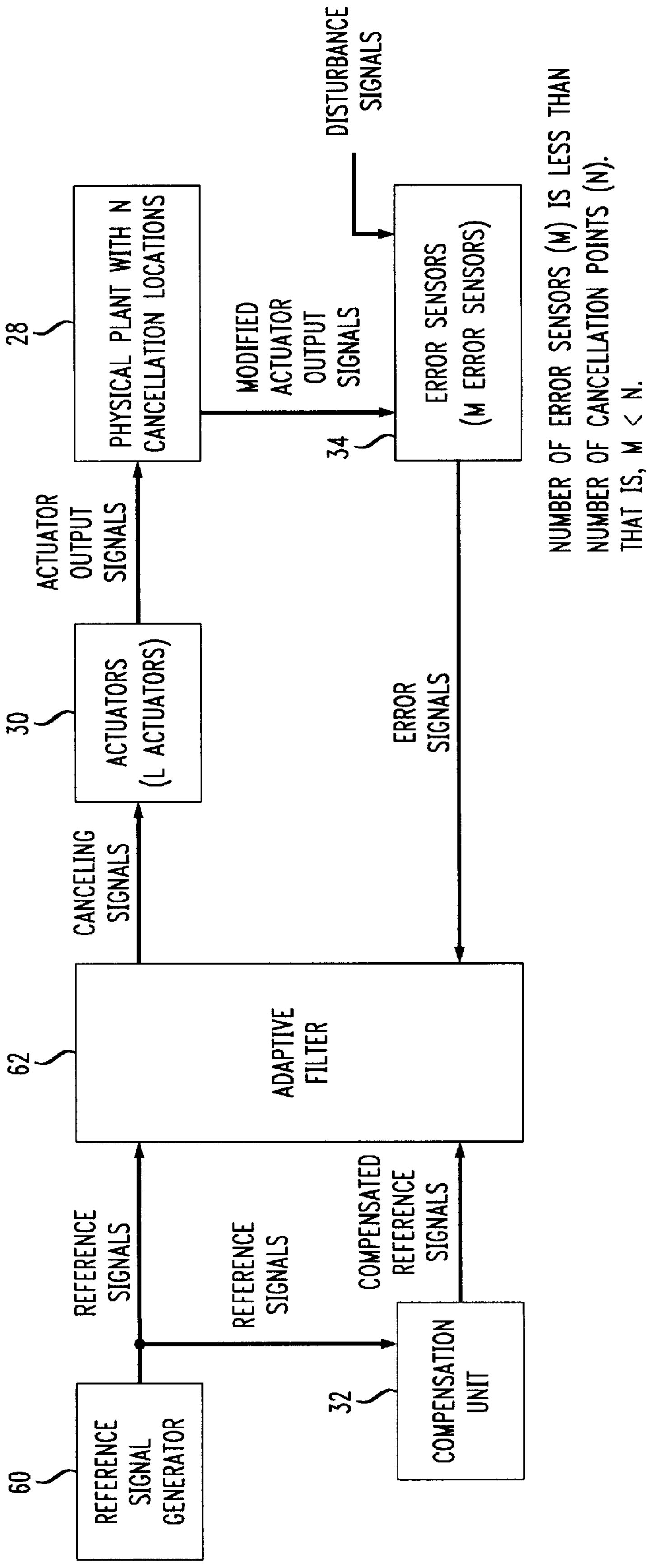
FIG. 6 is a block diagram of a multi-dimensional adaptive system (cancellation system) according to the first embodiment.

Referring to FIG. 6, the cancellation system described in FIG. 4 is illustrated with descriptive labels. The reference signal generator 60 generates K reference signals. The compensation unit 32 generates compensated reference signals based on the reference signals using a compensation transfer function. The adaptive filter 62 generates cancelling signals based on the reference signals, the compensated reference signals and the error signals. The adaptive filter 62 includes the adaptive filter 36 (FIG. 4) and the updating (FIG. 4). The actuators 30 generate actuator output signals based on the cancelling signals. The actuator output signals are transmitted into the physical plant 28, which can be a mechanical system, an air system, or another physical system. Error sensors 34 generate the error signals, which are received by the adaptive filter, based on the actuator output signals as modified by the physical plant and the disturbance signals ($D_1$–$D_M$ of FIG. 4).

I claim:

1. A cancellation system, comprising:

(a) a reference signal generator generating reference signals;

(b) a compensation unit generating compensated reference signals based on said reference signals;

(c) an adaptive filter generating cancelling signals based on said reference signals, said compensated reference signals from said compensation unit, and error signals;

(d) actuators generating actuator output signals based on said cancelling signals from said adaptive filter, said actuator output signals cancelling disturbances at cancellation locations in said physical plant having a physical plant transfer function; and (e) error sensors generating error signals based on disturbance signals and said actuator output signals from said actuators as modified by said physical plant, wherein the number of error sensors is less than the number of cancellation locations.

2. The cancellation system according to claim 1, wherein said compensation unit outputs said compensated reference signals to force said cancellation system to converge to a predetermined solution.

3. The cancellation system according to claim 2, wherein said adaptive filter comprises:

(a) an updating unit for generating updated signals based on said compensated reference signals and said error signals; and (b) an adaptive filter unit for generating said cancelling signals based on said updated signals from said updating unit and said reference signals from said reference signal generator.

4. The cancellation system according to claim 2, wherein said reference signals and said disturbance signals are coherent.

5. The cancellation system according to claim 2, wherein the number of actuators is less than the number of error sensors.

6. The cancellation system according to claim 2, wherein said error sensors are located at error sensor locations and said error sensor locations differ from said cancellation locations.

7. The cancellation system according to claim 2, wherein said actuators are located at actuator locations and said actuator locations differ from said cancellation locations.

8. The cancellation system according to claim 2, wherein said error sensors are located at error sensor location and said actuators are located at actuator locations differ from said error sensor locations.

9. The cancellation system according to claim 2, wherein said physical plant transfer function is a transfer function between said actuators and said cancellation locations; and wherein said compensation unit generates said compensated reference signals based on said reference signals received from said reference signal generator using a compensation transfer function, and said compensation transfer function is distinctly different from said physical plant transfer function.

10. The system according to claim 2, wherein said physical plant is a mechanical system.

11. A method for cancelling disturbances comprising the steps of:

(a) receiving reference signals;

(b) generating compensated reference signals from said reference signals using a compensation transfer function;

(c) generating cancelling signals from said reference signals, said compensated reference signals, and error signals;

(d) generating actuator output signals from said cancelling signals, said actuator output signals being transmitted in a physical plant to cancel disturbances at cancellation locations, said physical plant having a physical plant transfer function and cancellation locations, said physical plant transfer function distinctly differing from said compensation transfer function;

(e) receiving said actuator output signals as modified by said physical plant at error sensors in said physical plant;

(f) receiving disturbance signals at said error sensors in said physical plant; and (g) generating said error signals from said disturbance signals and said actuator output signals as modified by said physical plant, wherein said number of error signals is less than said number of cancellation locations.

12. The method for cancelling disturbances according to claim 11, wherein said reference signals and said disturbance signals are coherent.

13. The method for cancelling disturbances according to claim 11, wherein the number of actuator output signals generated is less than the number of cancellation locations.

14. The method for cancelling disturbances according to claim 11, wherein said compensation transfer function is Hermitian and positive definite.

15. A cancellation system, comprising:

(a) a reference signal generator generating reference signals;

(b) a compensation unit generating compensated reference signals based on said reference signals;

(c) an adaptive filter generating cancelling signals based on said reference signals, said compensated reference signals from said compensation unit, and transformed error signals;

(d) actuators generating actuator output signals based on said actuator signals from said adaptive filter, said actuator output signals cancelling disturbances at cancellation locations in said physical plant having a physical plant transfer function;

(e) error sensors receiving disturbance signals to be cancelled and actuator output signals from said actuators as modified by said physical plant, said error sensors generating error signals, wherein said number of error sensors is less than said number of cancellation locations;

(f) a transformation unit transforming said error signals to transformed error signals using a Hermitian transformational function.

* * * * *